United States Patent [19]

Cocatre-Zilgien

[11] Patent Number: 5,844,862

[45] Date of Patent: Dec. 1, 1998

[54] SKIN TEMPERATURE RADIO TELEMETRY AND ALARMS

[76] Inventor: Jan H. Cocatre-Zilgien, 802 East California Ave., Urbana, Ill. 61801-4342

[21] Appl. No.: 120,946

[22] Filed: Jul. 22, 1998

[51] Int. Cl.$^6$ .............................. G04B 47/00; A61B 5/04
[52] U.S. Cl. ................................ 368/10; 368/11; 368/47; 128/696; 128/736
[58] Field of Search ................................. 368/10, 11, 47; 128/696, 736

[56] References Cited

U.S. PATENT DOCUMENTS

| | | | |
|---|---|---|---|
| 1,175,262 | 3/1916 | Greiner ........................................ | 73/52 |
| 3,661,142 | 5/1972 | Flam ....................................... | 128/2 H |
| 3,938,387 | 2/1976 | Flesch ....................................... | 73/359 |
| 3,943,918 | 3/1976 | Lewis ..................................... | 128/2.1 A |
| 4,129,125 | 12/1978 | Lester et al. ........................ | 128/2.05 A |
| 4,151,831 | 5/1979 | Lester ...................................... | 128/736 |
| 4,178,916 | 12/1979 | McNamara ............................... | 128/734 |
| 4,321,933 | 3/1982 | Baessler ................................... | 128/736 |
| 4,450,843 | 5/1984 | Barney et al. ........................... | 128/690 |
| 4,475,158 | 10/1984 | Elias ........................................ | 364/413 |
| 4,503,862 | 3/1985 | Baessler ................................... | 128/736 |
| 4,509,531 | 4/1985 | Ward ....................................... | 128/736 |
| 4,747,413 | 5/1988 | Bloch ...................................... | 128/736 |
| 4,803,625 | 2/1989 | Fu et al. ................................... | 364/413 |
| 4,819,860 | 4/1989 | Hargrove et al. ........................ | 228/668 |
| 4,847,577 | 7/1989 | Gerhart et al. ........................... | 328/111 |
| 4,865,044 | 9/1989 | Wallace et al. ........................... | 128/736 |
| 4,904,997 | 2/1990 | Chen et al. .......................... | 340/870.17 |
| 5,033,864 | 7/1991 | Lasecki et al. .......................... | 374/151 |
| 5,050,142 | 9/1991 | Gibbs ....................................... | 368/11 |
| 5,174,656 | 12/1992 | Dotan ...................................... | 374/179 |
| 5,335,664 | 8/1994 | Nagashima ............................... | 128/696 |
| 5,365,494 | 11/1994 | Lynch ...................................... | 368/10 |
| 5,417,222 | 5/1995 | Dempsey et al. ........................ | 128/696 |
| 5,458,124 | 10/1995 | Stanko et al. ............................ | 128/696 |
| 5,634,468 | 6/1997 | Platt et al. ................................ | 128/696 |
| 5,764,542 | 6/1998 | Gaudette et al. ......................... | 364/574 |

OTHER PUBLICATIONS

Elcon (1995) "Temp–A–Sure(TM)" Owner's Manual and Directions for Use. Elcon America, 455 Delta Ave. Suite 205, Cincinnati, OH 45226. No Month.

Higgins et al. (1978) "Measurement of skin temperatures of active subjects by wireless telemetry". Aviat. Space, and Environm. Med., 49:1352–54. No Month.

Houdas & Ring (1982) Human Body Temperature. New York: Plenum Press. pp. 95–100. ISBN 0–306–40872–4. No Month.

McCreesh et al. (1996) "Vaginal temperature sensing using UHF radio telemetry". Med. Eng. Phys. 18:110–114. No Month.

Sirtrack (1988) Temperature Telemetry Web Page. Sirtrack Ltd., Goddard Lane, Private Bag 1403, Havelock North, New Zealand. No Month.

Solutions Cubed (1997) Manual for "Pocket Watch B" Miniature Engineering Module. 3029–F Esplanade, Chico, CA 95973. No Month.

Tukey (1977) Exploratory Data Analysis. Reading, PA: Addison–Wesley, pp. 210–11. ISBN 0–201–07616–0. No Month.

*Primary Examiner*—Vit Miska

[57] ABSTRACT

A temperature radio telemetry system combined with an alarm clock, intended for home settings. The alarm clock can be a digital alarm clock, or a radio alarm clock, or a computer running an alarm clock subroutine, devices nearly ubiquitous in private homes. The telemetry receiver is integrated with the alarm clock in a bedside enclosure, or is plugged in the parallel or serial port of the computer. The telemetry system principally detects the skin temperature elevation in infants and children with fever, especially at night, and subsequently triggers an alarm for the parents. The system can also detect the peripheral skin temperature drop in diabetic patients with early symptoms of hypoglycemia, or the small temperature rise associated with ovulation. The telemetry link has several fail-safe attributes, is operable without a license, and resists to interference by using a running median data smoothing method. The transmitter is simple, inexpensive, and child-safe. The receiver shares many common parts and functions with the alarm clock or the computer, and therefore becomes inexpensive enough to be affordable by any household.

19 Claims, 6 Drawing Sheets

SKIN TEMPERATURE RADIO TELEMETRY AND ALARMS

BACKGROUND

1. Field of the Invention

This invention relates to the general field of telemetry systems for monitoring temperature, more specifically to radiotelemetry devices monitoring skin temperature of feverish children in home settings.

2. Prior Art

Fever is a common and normal reaction to a number of ailments, primarily viral and bacterial infections. It is generally accepted that a mild level of hyperthermia actually helps fight infections. However, excessive fever is a clear source of discomfort for adults and children, and may create complications of its own, such as dehydration and febrile convulsions in infants. Fever often tends to get higher at night. In some cases the pharmacological effects of an antipyretic drug taper off during the night, so that a supplemental dose is necessary to keep a high fever in check.

As fever by itself rarely justifies hospitalization, it is managed at home, typically by the parents of a child with an otorhino-pharyngeal infection. Taking care of a febrile infant at night and at home is an emotionally straining and a tiring task for a parent, especially if the fever spans several days. First, it is difficult to take the "core" temperature (oral, axillar, rectal, or even aural) of a sleeping and febrile infant, without risking waking up the child. This may deprive the child of precious rest needed to help fight the infection. As a result, temperature is often only estimated by manually feeling the child's forehead. Second, the parents often spend sleepless nights, by being urged periodically to "check" on their child, and worrying about its well-being in-between.

The radio pacifier of U.S. Pat. No. 5,033,864 is an example of the quest for a way to monitor the temperature of children. However, in case of fever, a child may breathe fast and shallowly through the mouth and, depending on its state of hydration, provide erroneously cool temperature readings. A feverish child may not keep the pacifier in its mouth during the whole night. Also, in case of temperature within the normal range, the device does not transmit to save power; if for any reason it fails during such a quiescent mode, the failure would not be detected at the receiver end. Finally, pacifiers have themselves been implicated in the recurrence of infections.

A non-invasive method of monitoring fever is available by instrumentally monitoring skin temperature. Instruments specifically designed to measure skin temperature have existed since at least 1926 (U.S. Pat. No. 1,175,262). Normally the skin temperature is only indirectly linked to core temperature, but as a part of temperature regulation during a fever, the nervous system creates an active vasodilatation in the skin for use as a thermal radiator (Houdas & Ring, 1982). In case of fever, the skin will reach a temperature very close to that of the core temperature. The resulting elevation of skin temperature is easy to measure, but more difficult to communicate reliably and safely to the parents. Monitoring devices that use external wiring present real risks of electrocution and strangulation, and are therefore not an option for semi-unsupervised children in home settings.

The simplest approach for measuring skin temperature is the use of temperature-sensitive liquid crystals, in the form of commercially available patches to be affixed on the skin, generally on the forehead (U.S. Pat. Nos. 3,661,142; 4,747,413). These patches change color or display as a function of skin temperature. However, this method requires periodic inspection and sufficient ambient light to read them. The parents may indeed be reassured by mild temperature readings, but at the cost of repeated visual checks during the night.

A more elaborate approach for measuring skin temperature is the use of a computerized thermometer clipped to the rim of a garment facing the abdomen, marketed under the name of Temp-A-Sure(TM) (ELCON 1995). This accurate thermometer and data logger measures and displays numerically skin temperature every 5 minutes, and rings an alarm of short beeps for 15 seconds when it exceeds 37.8° C. (100° F.). However, there are problems in its operation:

Because it contains many components, the device is bulky, being 24 mm (nearly 1") thick. If the child is lying on it, it applies significant pressure on the skin, locally reducing its blood flow, and therefore its temperature, thus generating "false negatives". It can also detach itself more easily from the garment during the motions of a feverish and agitated half-sleeping child.

The alarm triggers for temperatures in excess of the fixed and relatively low value of 37.8° C. (100° F.). However, a child is likely to wear the device because of being feverish, that is often with an already elevated temperature baseline, so the alarm could be tripped repeatedly and unnecessarily during the night as "false positives". Furthermore, as the alarm is produced by the device itself, it would also disrupt the sleep of the child.

Monitoring temperature from another room of the dwelling requires the use of some intercom to hear the alarm. This adds one link and one more opportunity for failure to the chain of information transfer. Without intercom, a parent must remain in the same room as the sick child.

The method is not fail-safe, as the parents have no means of being warned by the alarm if the battery went dead, the device got damaged, detached itself from the garment, or if an intercom did not pick up alarm beeps muffled by some bed cover. It is this kind of "what if" knowledge which adds greatly to the normal anguish of the parents of a sick child.

A similar problem is encountered in diabetic patients who are prescribed drugs to lower their blood glucose levels. For a variety of reasons, these drugs can sometimes act too effectively and create a dangerous hypoglycemia that can lead to "insulin shock" and even death. Diabetic patients learn to recognize early symptoms of hypoglycemia, typically including cold sweats, and generally ingest sugars to counteract the overzealous effect of the drugs. However, when sleeping in their private homes, these patients may not be aware of any telltale symptoms and may then drift into a coma, unbeknownst to themselves or their family. Some wearable devices of the Prior Art (U.S. Pat. Nos. 4,178,916; 4,509,531) detect the lowering of skin temperature which is one symptom of hypoglycemia, and they trigger an alarm to alert patient or family.

Given its importance in animal and medical studies, temperature was one of the earliest, and is still, one of the most common parameters transmitted in wireless bio-telemetry systems comprising a transmitter and a receiver. For wildlife surveys, there are many commercially available transmitters (for example in the 148–220 or 450–470 MHz bands), used for animal tracking. Some of these produce a train of pulses whose interpulse interval, generally about 1 second, is a function of temperature (SIRTRACK 1998). However, because of their power output, type of modulation, or frequency, most of these transmitters would not comply with the rules and regulations of the national entity that regulates the allocation and use of radio frequencies, if used to transmit temperature data within a private household. In the United States of America, such entity is the Federal Communication Commission (FCC), publishing mostly in the Code of Federal Regulations (CFR). Furthermore, wildlife biotelemetry systems, especially receivers, are quite expensive.

Biomedical telemetry devices are commonly used in hospitals (for example in the 512–566 MHz band) to transmit many types of medical parameters, including temperature. However, their use is prohibited outside of hospitals (47 CFR 15.209g2). Other telemetry systems require either licensing by the user or emergency conditions, which would not comprise monitoring a simple fever at home (47 CFR 90.238h). Similarly, the simple skin temperature telemetry system described by Higgins et al. (1978) employs a squegging or blocking oscillator transmitter which would create significant and unacceptable interference because of its broadband characteristics, if it were not low-powered and limited to a broadcast range of a few feet. Many radio telemetry systems of the prior art do not address at all the problems of created and received interference.

The radio telemetry monitoring of infant skin temperature is not new, and can be considered to be in the public domain (for example U.S. Pat. No. 4,747,413). The temperature-sensing transmitter can be manufactured for a relatively low cost, and as a consequence, some transmitters of physiological data are even designed to be disposable (U.S. Pat. No. 3,943,918). These and the above-described radio transmitters require dedicated devices for receiving their radio waves, filtering and processing the signal, decoding the temperature information, displaying the temperature, and triggering alarms when this temperature exceeds some threshold. As a result, these receivers comprise many parts and are relatively complicated, that is, can be excessively expensive for their intended function. A high cost is justifiable for radio monitoring of EKG in case of a life-threatening heart condition, for example, but it is generally not justifiable for monitoring a simple fever. In general, no parent will purchase an expensive telemetry system to monitor the episodic fevers of a child, unless this child is subjected to repeated infections. This has hampered the marketing of temperature biotelemetry systems for the general public.

In a different domain, many alarm clocks are already associated with radio receivers. There are many designs of clock-radios or radio alarm clocks that receive commercial FM or AM broadcasts, generally with the option of being turned on automatically by the alarm system of the clock. Some alarms can be triggered by radio, for example upon reception of a special signal from the Emergency Alert System. Also, some clocks reset themselves automatically and precisely with a built-in radio receiver tuned to the signals from land-based or satellite transmitters broadcasting "atomic clock" time. Finally, alarm clock devices are used in some medication dispensers, beeping an alarm or even opening some pill container when it is time to take another dose of a medication.

SUMMARY OF THE INVENTION

A temperature radio telemetry and alarm system that is safe, fail-safe, simple, accurate, interference-resistant, operable without license, but of relatively low cost by being combined with an ubiquitously needed object such as a bedside alarm clock, an alarm clock radio, or a computer running an alarm clock subroutine. The telemetry and alarm clock of the present invention makes temperature telemetry affordable for any household. When skin temperature is the telemetered variable, its main application in private home settings is primarily the monitoring of fevers in children, or that of hypoglycemia symptoms in diabetic patients.

OBJECTS AND ADVANTAGES

It is the general object of the invention to provide a performant, robust, and safe, yet in expensive temperature monitoring system which avoids the disadvantages of prior temperature biotelemetry systems while affording additional functional advantages.

Although the telemetry system of the present invention consists of two physical components, a temperature sensitive radio transmitter, and a dual-function telemetry radio receiver combined with an alarm clock, its main advantage is reduced cost per individual function, as will be apparent below. The temperature transmitter itself generally consists of very few and ubiquitous parts apart from an inexpensive transmitter module ($5.60 even in unitary quantity). As a result, the transmitter can be manufactured inexpensively, and can even be envisioned as disposable. The naturally more complex receiver is integrated with an alarm clock, instead of being a dedicated stand-alone device. As can be seen in the Table I, a typical alarm clock already comprises most of the components necessary for the temperature alarm telemetry of the present invention. That is, for the relatively low cost of adding a telemetry receiver module and the associated signal processing circuitry to an alarm clock, one obtains a device with two functions, with an average lower cost per function than if each were stand-alone devices.

TABLE I

|  | Bedside Alarm Clock | Temperature Alarm Telemetry |
| --- | --- | --- |
| compact bedside enclosure | YES | desirable |
| circuitry keeping time | YES | YES |
| display of time numerals | YES | — |
| display of temperature numerals | — | YES |
| set-up buttons or switches | YES | YES |
| back-up fail-safe battery | often | YES |
| loudspeaker or buzzer | YES | YES |
| telemetry radio receiver | — | YES |
| signal processing circuitry | — | YES |

Moreover, the combination of the two functions is not only economical, but mutually complementary as well, during the monitoring of a fever. The same device can be used to alarm the parent of an abnormal temperature, and to alarm the parent of the time of night when it is necessary to administrate a medication, for example. Some antipyretic, anti-inflammatory, and other drugs have a short pharmacokinetic life in the bloodstream; evenly spaced dose administration may help prevent the fever from flaring up. A parent prone to worry may also use the alarm clock function to be woken up at a predetermined time during the night to check on the child in person. Naturally, the telemetry alarm clock can also be used as a plain alarm clock to wake up the parent normally every morning, with the temperature telemetry functions in stand-by. In other words, the parents will use the alarm clock or radio alarm normally for weeks on end, until need arise to monitor the temperature of their child, time at which they will activate the telemetry system.

A very significant advantage of the telemetry system of the present invention is its fail-safe operation for monitoring fevers. If the skin temperature transmitter is made inoperative by some impact damage, by a fluid leak, by a broken antenna, by a low-voltage or dead battery, or any other cause interrupting the transmission of temperature data, the condition is detected at the receiver end, and an alarm triggered. The same occurs if too much radio interference is present, or if the quality of the radio transmission drops, such as with a folded antenna. At the receiver end, a back-up battery ensures that the alarm is operational should the household electrical power be interrupted, for any reason. Also, the user-adjustable temperature alarm setting is possible only within a predefined range to ensure high fever detection, should that alarm be set erroneously. The knowledge that the operation of the system is fail-safe contributes significantly to the quality of sleep of the parents.

A further advantage of the system is that it is child-safe. It is wireless, meaning that the risk of strangulation and electrocution is eliminated. The temperature transmitter is generally flat with rounded and smooth edges, and does not exert physical discomfort while providing good quality data collection. Its antenna, if of the wire type, is too short to present a strangling hazard. Its battery is purposely too large a diameter so as to reduce the choking hazard, should it be accidentally released from its holder and put in the mouth before parents are warned by the loss of transmission alarm. The transmitter may be coated with an hypo-allergic finish. The radio-frequency irradiation of very short pulses of less than 1 mW, every half-minute or so, is an insignificant biohazard, several orders of magnitude less than by using a walkie-talkie or a cellular phone.

A significant advantage of the temperature monitoring system of the present invention lies in its option of using computer port plug-in receiver embodiments. Practically all computers, including the portable, laptop, or even palmtop types, possess some form of parallel or serial port, or both. Computers already possess the above-said attributes of an alarm clock (Table I). Such computers are found in a large and rapidly growing number of households and can run alarm clock programs concurrently with those processing temperature information. Owing mostly to its low part count and simple design, the cost of a plug-in temperature receiver is significantly cheaper than that of a stand-alone device, and cheaper than a combined temperature receiver and alarm clock.

A real advantage of the telemetry system of the present invention is the legality of its operation, a topic often shunned by manufacturers of telemetry devices. The system of the present invention is compliant with the rules and regulations of the FCC for license-free operation in private home settings. A first condition for such operation is that the "device may not cause harmful interference" (47 CFR 15.19a3). The practical range of the transmitter is in the order of 30 m (100 feet), which is within the boundaries of most houses or apartments, especially considering absorption by the peripheral walls of the dwelling. Also, the transmission of a short pulse separated by long periods of about 30 seconds would not interfere with the operation of a neighbor's garage door opener operating on the same frequency, for example. A second condition for operation is that the "device must accept any interference received, including interference that may cause undesired operation" (47 CFR 15.19a3). Unlike hospital telemetry systems, the device of the present invention generally shares frequency with many other transmitters, such as remote controls, garage door openers, wireless alarms, satellite pagers, or other telemetry systems. However, a special technique of data smoothing eliminates out-of-bounds readings. As a result, the system of the present invention is relatively immune to interference, including either false negatives or false positives.

BRIEF DESCRIPTION OF THE DRAWINGS

1A First transmitter schematics
1B Second transmitter schematics
2A Transmitter general arrangement
2B Parallel port receiver view
2C Serial port receiver view
3A Parallel port receiver schematics
3B Serial port receiver schematics
4A Bedside alarm clock & receiver synoptics
4B Bedside alarm clock & receiver view
5 Flow-chart of receiver—clock program
6A Raw data signal period plot
6B Smoothed temperature data plot

LIST OF REFERENCE NUMERALS 10 temperature transmitter
10A first variant of 10
10B second variant of 10
11 astable multivibrator
12 timing capacitor
13 temperature sensor
14 one-shot monostable
15 active low thermal switch
16 transmitter RF module
17 transmitting antenna
18 transmitter battery
19 manual on-off switch
20 active high thermal switch
21 single NOR gate
22 magnetic reed switch
23 Printed Circuit Board
24 transmitter battery holder
25 securing hole
30 computer port receiver
30A parallel variant of 30
30B serial variant of 30
31 parallel port connector
32 computer parallel port
33 household computer
34 receiver RF module
35 receiving antenna
36 antenna cable
37 low dropout diodes
38 optional battery
39 battery connector
40 voltage regulator
41 reversal protection diode
42 regulator protection diode
43 current limiting resistor
44 parallel adapter housing
45 securing suction cup
46 securing clip
50 serial port connector
51 protecting diodes
52 op-amp comparator
53 low-dropout regulator
54 N.C. jack switch
55 external power jack
56 serial adapter housing
60 alarm receiver & clock
61 microcontroller
62 household plug
63 AC/DC converter
64 back-up battery 65 real time module
66 manual input device
67 visual display
68 sound-producing unit
69 alarm receiver enclosure
70 transmitter receptacle
71 receptacle cover

DESCRIPTION

The description proceeds by that of two variants A and B of a temperature transmitter 10, then by that of two variants A and B of a temperature receiver 30 to be plugged in a port of a computer running an alarm clock program, and finally by that of a stand-alone temperature receiver and alarm clock 60. The term "alarm clock" is defined herein as any device that gives the time of day, has a settable alarm time, and can sound an alarm when the time of day reaches the set alarm time. The alarm clock can be not only a typical bedside digital type, but an alarm clock program or subroutine running on a computer.

Description of the temperature transmitters

Figure 1A:
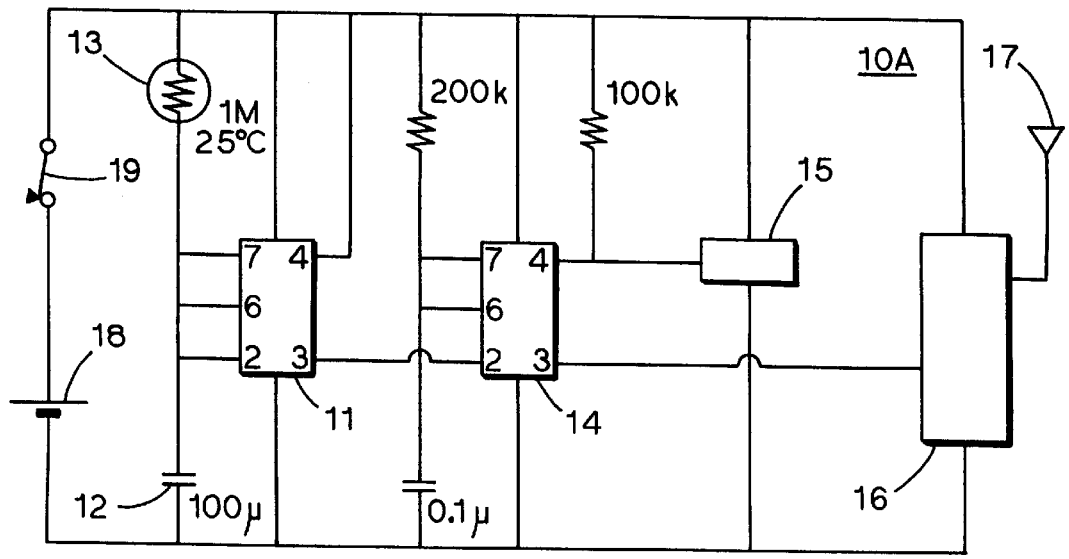

Referring to FIG. 1A, the electronic schematics for a first temperature transmitter 10A are described. An astable multivibrator 11 such as a CMOS 555 timer generates a train of pulses function of the constant value of a timing capacitor 12, preferably of the tantalum type, and of a temperature sensor 13, here a Negative Temperature Coefficient (NTC) thermistor, which is to be in contact with the skin of a subject. Residual resistance between pins 7 and 6 & 2 is sufficient to give a 5 ms width to the negative pulses produced as output on pin 3. At 25° C. (77° F.), the period of such output pulses is relatively long, of the order of 70 seconds (calculations will be detailed in the Operation section). A single-shot monostable 14, such as a second CMOS 555 timer, produces a positive pulse each time it receives a pulse from astable 11. With component values depicted in FIG. 1A, the duration of such positive pulses is about 20 ms. This mode of transmission is well within the FCC limitations (47 CFR 15.231e) which state that "the duration of each transmission shall not be greater than one second and the silent period between transmissions shall be at least 30 times the duration of the transmission but in no case less than 10 seconds". Such long-period transmissions allow more legal power to be used than in continuous transmissions. Should it be required by the FCC, a tiny temperature switch such as a MAXIM 6501 (open drain, low when hot) disables the pulse production ability of monostable 14 when its temperature exceeds some fixed value above that of highest fevers, such as 55° C. (131° F.), at which the 10 second limit may be reached. Finally, a miniature Radio-Frequency (RF) transmitter module 16, such as a LINX TXM-418-LC, transmits the pulses via antenna 17, here on 418 MHz. A lithium battery 18 of relatively large size, such as the ubiquitous coin battery 23 mm (0.9") diameter, provides electrical power for transmitter 10A, upon actuation of a manual miniature on-off switch 19. With low consumption electronic components, the battery can continuously power the transmitter for several weeks.

Figure 1B:
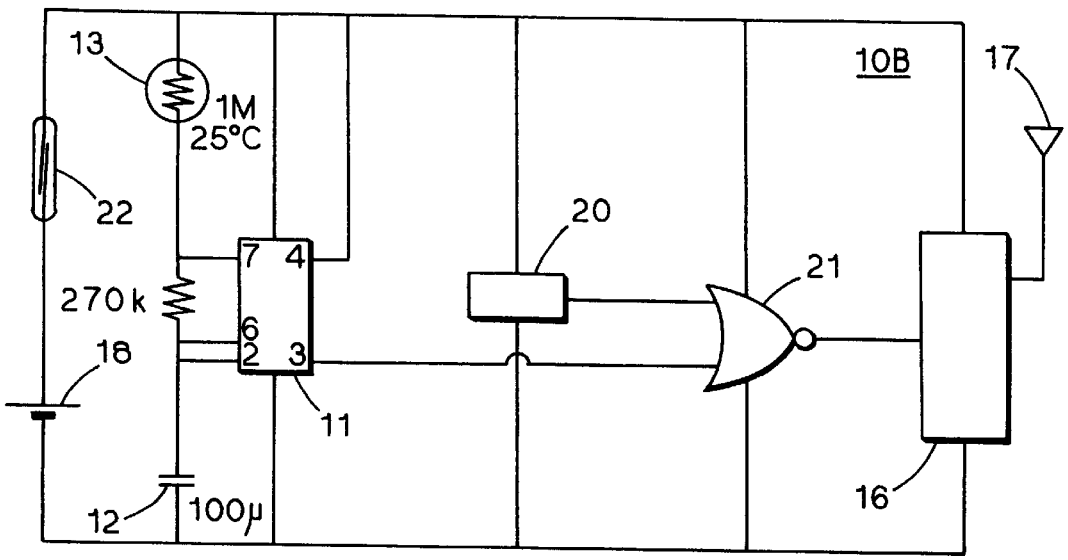

Referring to FIG. 1B, the electronic schematics for a second and preferred temperature transmitter 10B are described. Transmitter 10B is different from transmitter 10A in that a single CMOS 555 performs the functions of astable 11 and of monostable 14 (in FIG. 1A). Should it be required by the FCC, a tiny temperature switch 20, such as a MAXIM 6502 (push-pull, high when hot), is combined with the pulses produced by astable 11 through a NOR gate 21, such as a FAIRCHILD TinyLogic NC7S02. Positive pulses outputted by gate 21, about 18.7 ms duration with the components shown, are fed to transmitter module 16 as described previously. A sealed reed type switch 22 turns the transmitter off in the presence of an appropriate magnetic field.

Figure 2A:
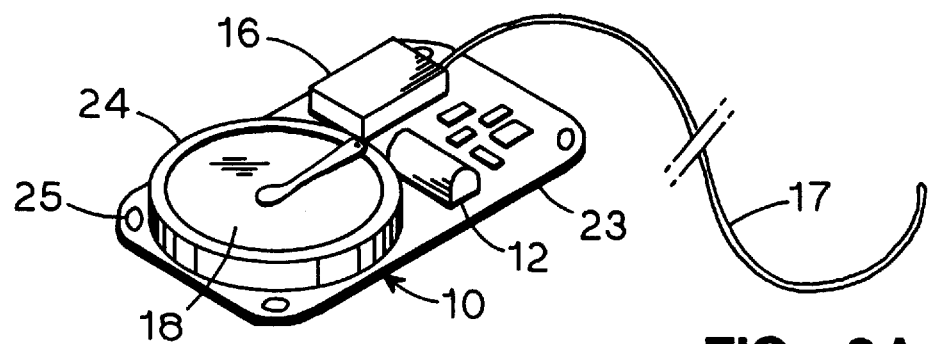

The general arrangement of temperature transmitter 10 (either version 10A or 10B) is shown in FIG. 2A. Most of the transmitter electronic parts are soldered as surface mount components onto the top coppered surface of a single side printed circuit board (PCB) 23 as shown. Prominent among such components are a battery holder 24 to hold battery 18 (23 mm diameter), followed by radio transmitter module 16 (13×9.5×3.8 mm), and the relatively large capacity timing capacitor 12. Apart from battery compartment 24 and eventually an on-off switch (not shown), the whole top surface is covered with a suitable waterproof protective coating (not shown). Temperature sensor 13 (not visible) is positioned approximately at the center of the bottom copperless surface of PCB 23, with its leads reaching the coppered traces on the top surface through holes in PCB 23. The relatively wide area surrounding sensor 13 helps limit its own pressure on the skin when the bottom surface of PCB 23 is applied onto the subject. The overall dimensions of temperature transmitter 10 are less than 50 mm by 30 mm, and less than 6 mm thick, excluding antenna 17. If temperature transmitter 10B is marketed as a disposable device, the whole unit, battery included, may be coated with a waterproof hypoallergic finish. Lithium batteries generally have a shelf life of 10 years. Holes 25 may be used for securing the transmitter to a garment such as a diaper with clips, pins, wires, ties, or Velcro(R) material.

Description of temperature receiver embodiments

Figure 2B:
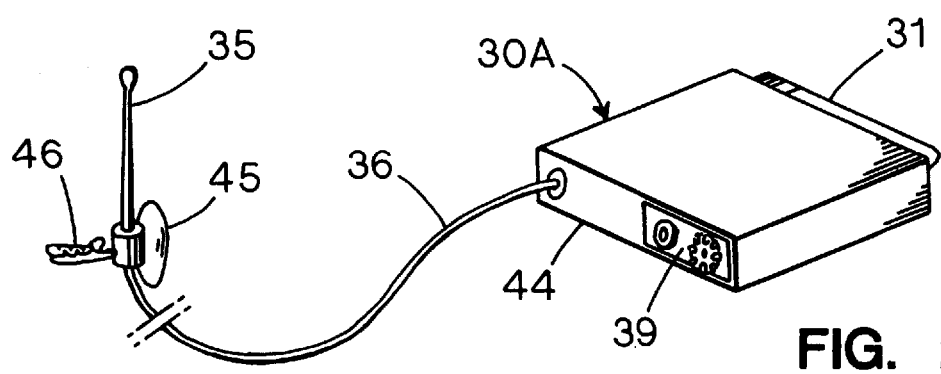
Figure 2C:
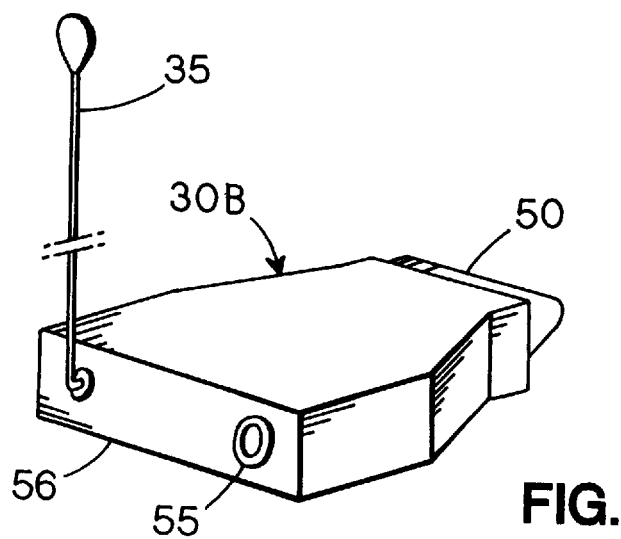

Several types of temperature telemetry receivers are described, first a plug-in version 30 for the port of a computer running an alarm clock program, in two variants 30A and 30B shown in FIGS. 2B and 2C, then a stand-alone alarm clock and temperature telemetry receiver 60.

Parallel port version

Figure 3A:
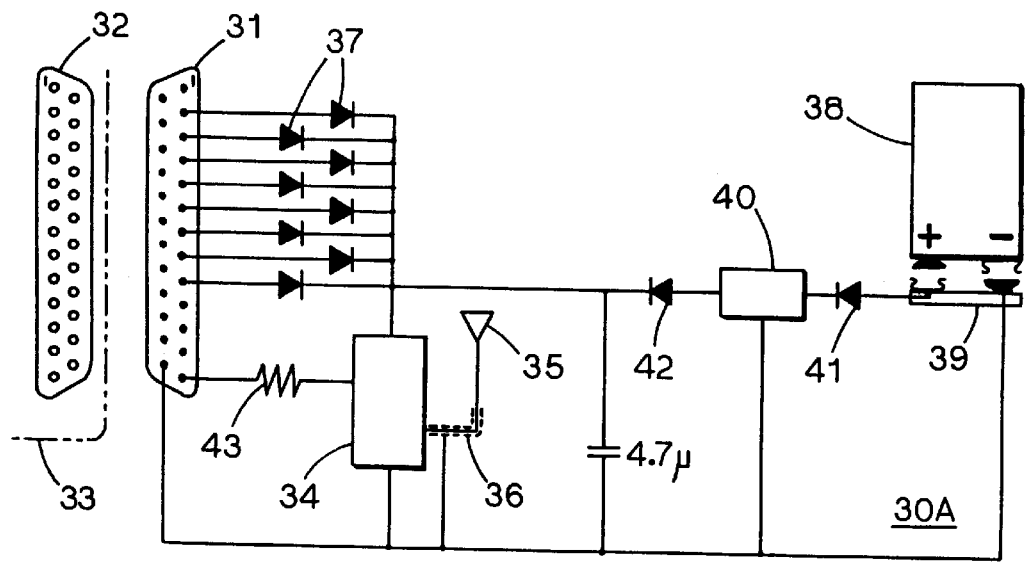

Referring to FIG. 3A, the electronic schematics for plug-in parallel port temperature receiver 30A are described. Receiver 30A is to be plugged via a connector 31 (type DB25M shown) into a parallel port 32 (type DB25F shown) commonly found on a computer 33 to interface with printers and other ancillary equipment, with said computer running a custom alarm clock program (detailed below). A low-power RF receiver module 34, such as a LINX RXM-418-LC, receives the electromagnetic signal transmitted by a temperature transmitter (FIGS. 1A–B, 2A), via an antenna 35 and an antenna cable 36, and outputs either a logic high or low voltage in accordance with that signal. Receiver module 34 is powered by setting and maintaining all 8 bits of TTL output byte high in parallel port 32, and combining them together through low-dropout diodes 37 such as germanium diodes. In case parallel port 32 is unable to provide sufficient voltage and/or amperage to receiver module 34, electrical power may be supplied by a battery 38 (typical 9V shown), plugged into a battery holder 39 Battery voltage is fed to a voltage regulator 40 through a diode 41 protecting said regulator against accidental battery polarity reversals. Output of regulator 40 is protected from that of parallel port 32 by a diode 42. Regulator 40 may already comprise built-in diodes 41 and 42. Regulator 40 may be set or chosen to maintain a voltage higher than required by module 34 to compensate for the voltage drop in diode 42. Module 34 sends the received temperature signal to parallel port 32 and computer 33 via one of the "printer status" pins (such as ACKnowledge, BuSY, PaperEnd, SELect, or ERRor), eventually through a current limiting resistor 43.

Referring back to FIG. 2B, the general arrangement of parallel port receiver 30A is shown. The few electronic parts depicted in FIG. 3A fit easily within a hood or housing 44 of connector 31, except for battery holder 39 and antenna cable 36 as shown. Antenna securing devices such as a suction cup 45 or a clip 46 or both (as shown) allow positioning of antenna 35 for best reception. To limit possible TTL voltage drop in extension cables, receiver 30A benefits from being plugged directly into port 32 of computer 33.

Serial port version

Figure 3B:
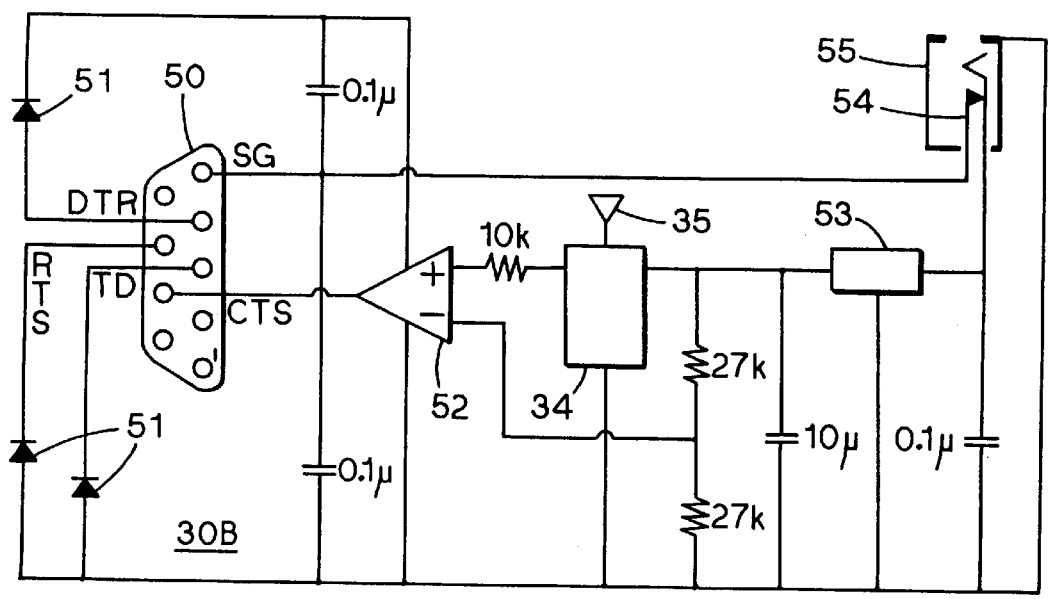

Referring to FIG. 3B, the electronic schematics for a plug-in serial port temperature receiver 30B are described. Receiver 30B is to be plugged via a connector 50 (DB9F shown) into a RS-232 serial port commonly found on a computer (not shown), with said computer running a custom alarm clock program (detailed below). The pin-out is detailed in FIG. 3B for a DB9 interface, but other physical interfaces (DB-25 or other) are usable as long as the RS-232 protocol is respected in the following.

A DTR (Data Terminal Ready) pin is set by software to a positive voltage, of the order of +10 Volts, through a protecting diode 51. This voltage is applied to the positive supply of an operational amplifier such as a "741" configured as a voltage comparator 52. A RTS (Request To Send) pin is set by software to a negative voltage, of the order of −10 Volts. A TD (Transmit Data) pin asserts a negative voltage, also of the order of −10 Volts in the absence of any serial data transmission, which will always be the case in this embodiment. These two negative voltages are combined via supplemental protecting diodes 51 and applied to the negative supply of comparator 52, to the ground pin of a low-power receiver module 34, and to that of a low-dropout voltage regulator 53. A SG (Signal Ground) pin is at a positive level relative to the aforementioned negative voltage and is applied to the input of regulator 53 via a Normally Closed switch 54 in an external power jack 55. In case the serial port is unable to provide sufficient voltage and/or amperage to regulator 53, an external power supply such as a battery (not shown) can provide the necessary power via a polarized plug connected to jack 55. In that case, switch 54 will open and isolate the SG pin from the circuit. The output of regulator 53 powers receiver module 34 and a voltage dividing resistance network used as reference by comparator 52. The radio temperature signal obtained by receiver module 34 via antenna 35 is fed to comparator 52, which outputs it to a CTS (Clear To Send) pin, to be read by the computer. As shown, upon reception of a signal high from receiver module 34, the comparator will output a positive voltage of approximately the same value as provided by DTR, and upon a signal low a negative one of approximately the same value as provided by RTS and TD.

Referring back to FIG. 2C, the general arrangement of serial port receiver 30B is shown. The electronic parts depicted in FIG. 3B fit within an adapter housing 56 for connector 50, except for a semi-flexible antenna 35 and jack 55 as shown. As the relatively large RS-232 voltages allow it, extension cables can be used between computer and receiver 30B, so that the latter may be positioned for best reception.

Bedside Digital Alarm Clock (preferred embodiment)

Figure 4A:
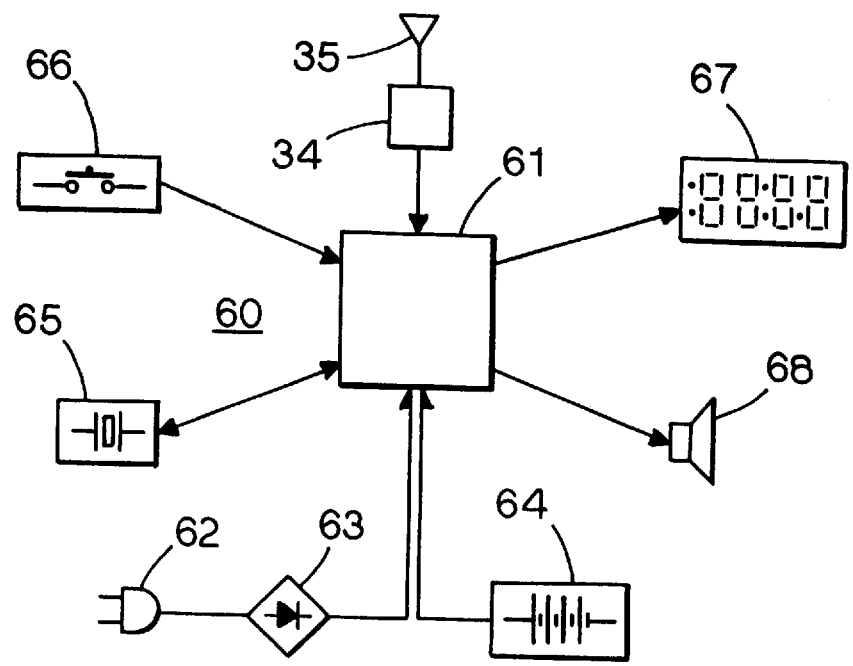

Referring to FIG. 4A, the synoptics for a stand-alone temperature telemetry receiver and alarm clock 60 are described. A digital microcontroller 61 is at the hub of the device. It is functionally connected to a plurality of items listed hereinbelow, possesses some memory, and can run computer programs. A plug 62 for a household electrical outlet and an AC/DC converter 63 normally provides power to alarm receiver & clock 60. Should household electrical power fail, a back-up battery 64, either of the primary or of the rechargeable type, provides enough power for all the functions of alarm receiver & clock 60 for at least the duration of one night. A real-time clock module 65 comprising an oscillator or resonator, for example a Pocket Watch (SOLUTIONS CUBED 1997), keeps the time of day and can communicate with microcontroller 61. Some microcontrollers already comprise onboard timers that can perform the same function, and use the same digital clocking system both for their own digital operation and for timekeeping purposes. An input device group 66 comprising buttons, switches, keys, touch-screen sensors, or dip-switches allows the user to set the time of day, to set the alarm time, to set the high temperature alarm, to set the low temperature alarm, to change the status of device 60, and to stop eventual alarms. As described in the plug-in embodiments, receiver module 34 receives the radio signal transmitted by a temperature telemetry transmitter through antenna 35, and sends it to microcontroller 61, which decodes it into an actual temperature (see Operation below). A visual display 67 such as LCD or LED numeric or alphanumeric displays or screens, shows simultaneously or sequentially the time of day and the telemetered temperature, and can show alarm settings and current status conditions. A sound-producing unit 68, such as a vibrator, loudspeaker, bell, or buzzer can be activated by microcontroller 61. Telemetry receiver and alarm clock 60 can also be equipped with an external alarm relay or generate a carrier current signal via plug 62 to trigger secondary remote alarms (not shown).

Figure 4B:
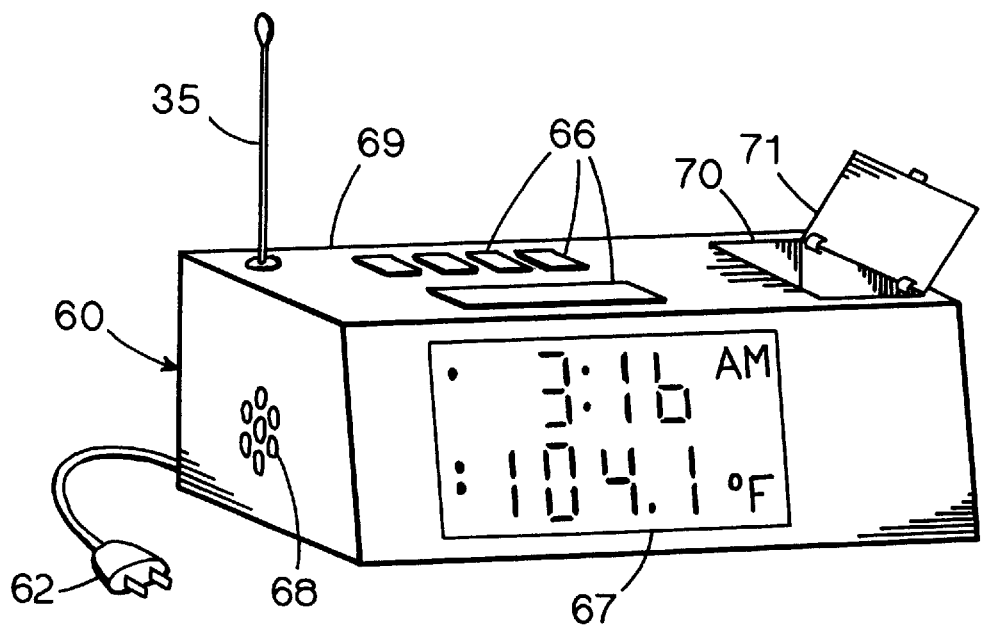

The general arrangement of telemetry receiver & alarm clock 60 is shown in FIG. 4B. Practically all units depicted in FIG. 4A fit within a bedside enclosure 69, as shown. Appended or embedded in enclosure 69 is a receptacle 70 destined to hold temperature telemetry transmitter 10 when not in use, under an openable cover 71. Two events occur when transmitter 10B (FIG. 1B) is placed in storage in compartment 70. First a magnet (not shown) within enclosure 69 opens the magnetically actuated reed switch 22 of the transmitter to turn the temperature transmitter off. Second, a contact switch (not shown) also within enclosure 69, informs microprocessor 61 that it does not need to run the temperature alarm algorithm of its program, and in this case temperature and alarm clock 60 performs like a standard alarm clock. Telemetry receiver and alarm clock 60 can be further combined in the same enclosure with an AM/FM broadcast receiver as in typical a clock radio (not shown) to share even more common components. Receptacle 70 may also comprise an automatic electrical connection to recharge battery 18, if the latter is of a rechargeable type, when transmitter 10 is docked in the receptacle.

OPERATION

All of the above-listed components 61 to 68 of a stand-alone telemetry receiver and alarm clock 60 can be already found in a typical portable computer 33 equipped with a plug-in telemetry receiver 30. There is a conceptual similitude between microprocessor and microcontroller, computer battery and back-up battery, clock module and system timer (for example 18.2 Hz on PCs), keys and buttons or switches, screen and digital display, and loudspeaker and buzzer. As a consequence, the operation which will be described in detail for the stand-alone embodiment of the present invention will essentially be the same, and will not be repeated, for the computer port plug-in embodiments. Also, the operation will be described for skin temperature elevation caused by fever in children but applies with minor modifications to skin temperature drops caused by hypoglycemia in diabetics. For example, a transmitter to detect fever is best placed proximally, one to detect hypoglycemia distally.

As with any bio-medical device, each transmitter 10 is to be tested thoroughly prior to release to the general public. During that Quality Control phase, even with high accuracy transmitters (SIRTRACK 1998), the transmitter temperature pulse duration and period are characterized, and the receiver program is eventually calibrated so as to obtain an accuracy of a fraction of a degree Celsius or Fahrenheit. The pulse duration selected herein is about 20 ms long, so as to be longer than 1 or 2 ms long pulses used in remote controls, and shorter than pager beepers. Furthermore, prescanning of the intended frequency of operation can reveal best pulse durations to use for a given frequency (47 CFR 15.17).

For most days and weeks, telemetry receiver and alarm clock 60 is used as a plain alarm clock. However, upon a suspected or an actual fever in a infant, in the typical situation presented earlier, a parent simply removes temperature transmitter 10 from its storage 70. This automatically turns on the transmitter, and activates the temperature monitoring functions of the microcontroller program The alarm sounds briefly to check that it is operational. The parent eventually sets the time alarm at which some medication may be required during the night. The parent then secures transmitter 10 onto the skin of the child, with garment clips, biocompatible glue, tape, or other means, and needs only to remain in the vicinity of the alarm clock receiver for the duration of the night to be safely informed of the child's temperature condition. The receiver can be located in a different room than that of the child's, in particular the parents' bedroom.

Figure 5:
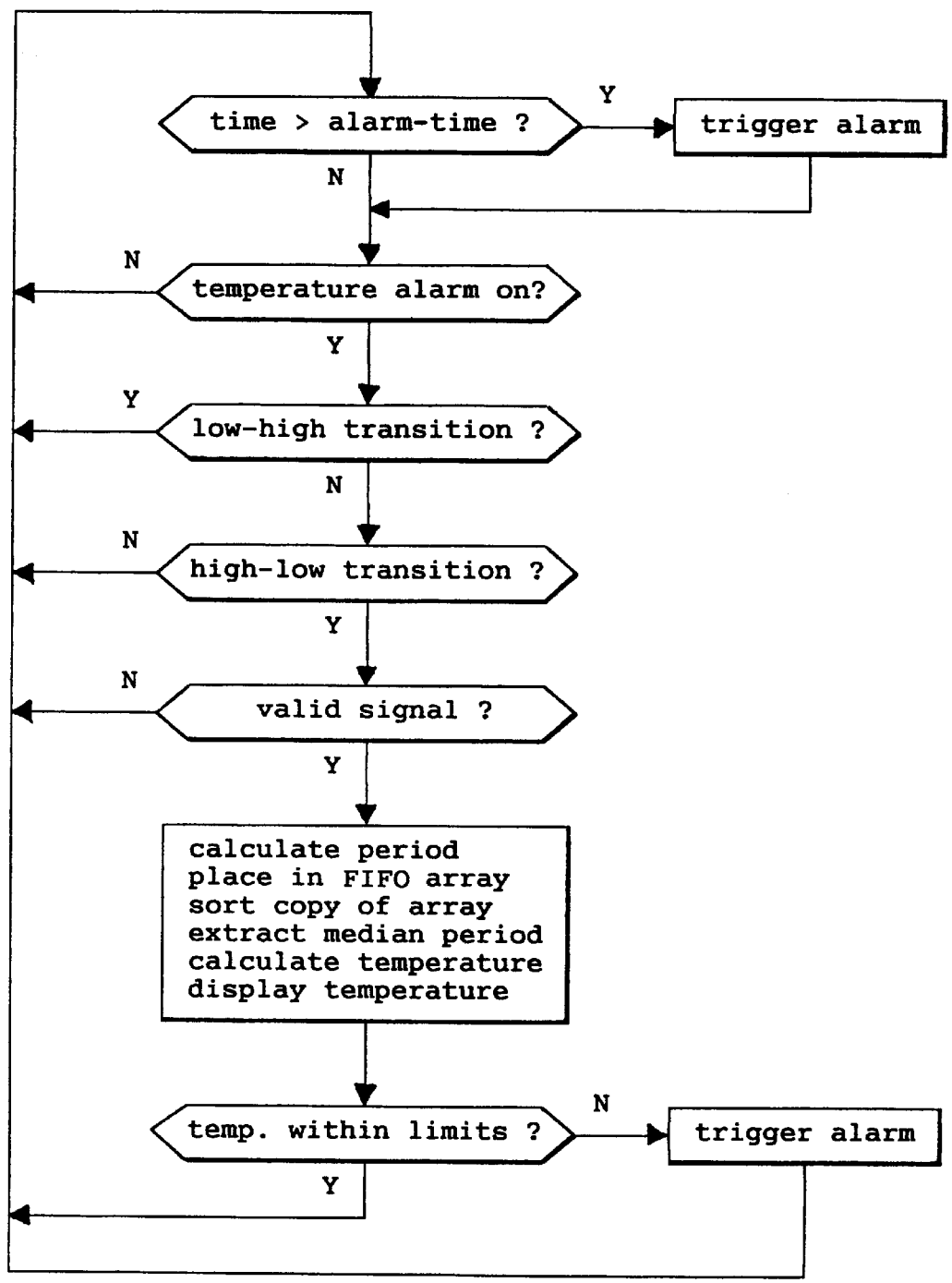

Referring to FIG. 5, the flow-chart of the main loop of program run by microcontroller 61 is described. From top to bottom, the first task is performing the basic alarm clock function. If the time of day exceeds set alarm time, alarm is triggered and sounds until the user stops it. If the temperature monitoring is not activated, the program loops again from there (shortest loop). Otherwise, the second task is the detection of a valid signal, defined herein as a pulse of appropriate duration, as sent by temperature transmitter. Detection is based on waiting for the appropriate transitions of the output of receiver module. Such transitions can be detected by polling, which is accurate enough given the long time the program generally spends performing abbreviated loops. They can also be detected by using interrupts, which are available on many microcontrollers as well as on computer ports. If a low to high transition is detected, a pulse duration variable is reset to zero. If subsequently a high to low transition is detected, a complete pulse has then been detected. If the duration of that pulse fits within preset limits, either real time limits if millisecond resolution is available, or simply the number of times the program loops were run, the signal is said to be valid. However, a valid signal does not necessarily come from the temperature transmitter, as will be seen now.

Still referring to FIG. 5, the third task is the rejection of spurious data, both the false positives, that is pulses of unknown origin but happening to be of the correct duration, and the false negatives, that is valid pulses temporarily masked by interference or accidentally blanked out by some other transmission on the same frequency. To do so, a running median of (2N+1) periods is used (Tukey 1977), with N generally varying between 1 and 4 depending on the local interference level. This relatively uncommon method for smoothing data here lends itself ideally to filtering out irrelevant periods. Temperature changes slowly enough that several consecutive measures are somewhat redundant and quite a few can be discarded. This is unlike running average or cumulative sum methods (U.S. Pat. Nos. 4,475,158; 5,764,542), which furthermore require time-consuming floating-point calculations. The period of the signal is calculated and entered in an odd-number First-In First-Out queue circular array A copy of this array is sorted and the median value is retained as the period encoding the temperature measured by the transmitter.

Finally, the fourth task is the calculation of temperature. In FIGS. 1A–B, the resistance R (in Ohms) of thermistor 13 as a function of temperature pulse period P (in s) and capacitance C (in F) of timing capacitor 12 is of the form $R=(P-Constant)/(0.693*C)$. Next, the temperature T (in Kelvin) of thermistor 13 is given by the Steinhart-Hart equation $(1/T)=a+b*Ln(R)+c*[Ln(R)]3$, with a-b-c depending on the particular thermistor used. This formula can be greatly simplified for microcontrollers without floating-point computing ability when only a narrow but biologically significant temperature range is to be accurate. The temperature is finally converted in Celsius or Fahrenheit units. If the temperature is above a high threshold (high fever) or below a low threshold (data transmission problem), an alarm is triggered and sounds until the user stops it. The pitch or pattern of the alarm can vary with the intensity of the fever, and with the type of alarm involved (time, fever, or contact lost). If the alarm sounds through a loudspeaker, the latter can also be used to communicate the temperature aurally to the parent, via synthetic or recorded voice. A loudspeaker can furthermore provide prerecorded advice on how to deal with a high fever, in accordance with recommended medical practice.

Figure 6A:
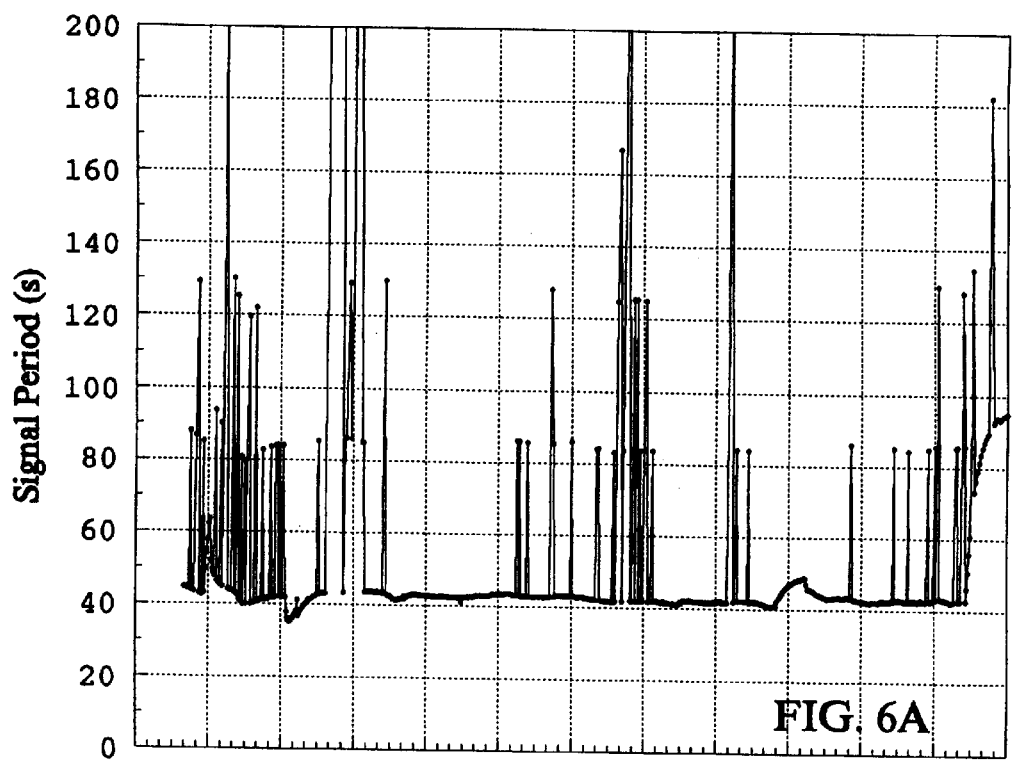
Figure 6B:
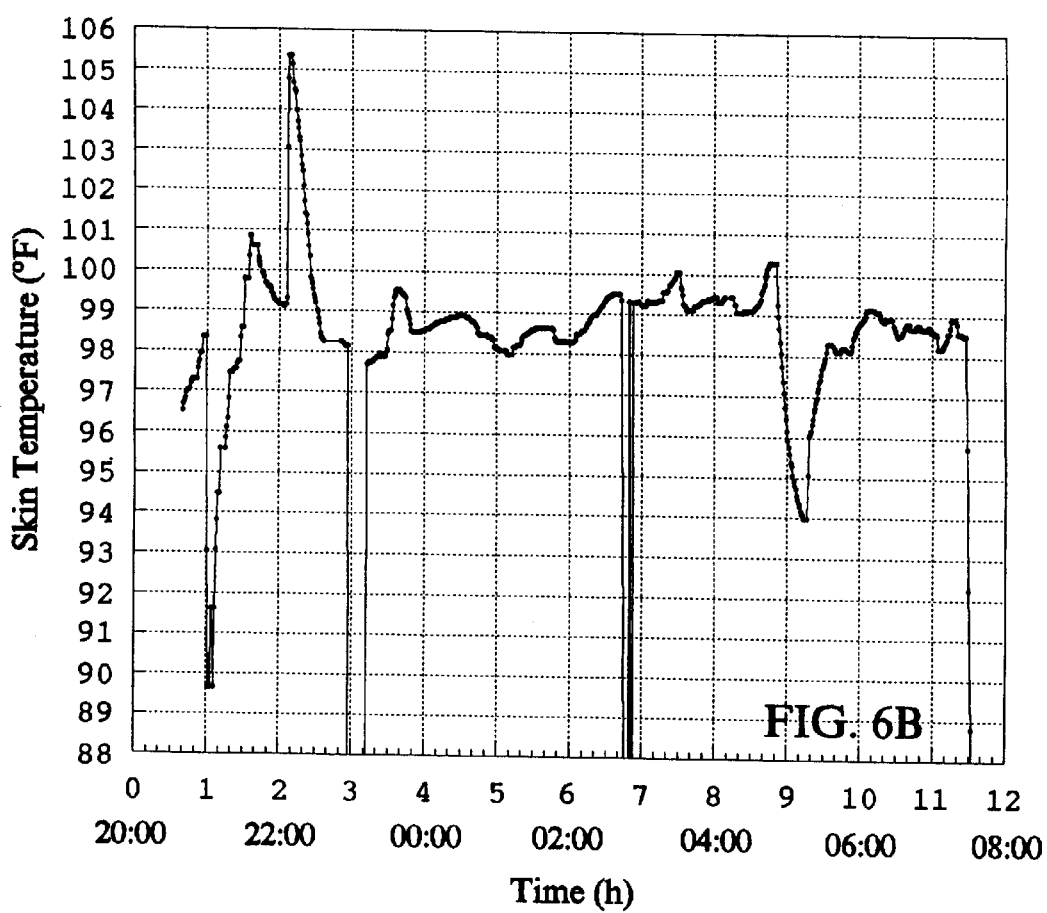

Referring to FIGS. 6A and 6B, a whole night of skin temperature data, recorded in real-life conditions, are plotted against time, including local time. The subject was a 19 month old girl on the trailing edge of a rhinopharyngitis, who was feverless at bedtime. A temperature transmitter of the type of FIGS. 1A/2A was attached to the inner part of a diaper facing a parasagittal area of the abdomen. A receiver of the type of FIGS. 2B/3A was plugged in the parallel port of a 8 MHz INTEL 8088-based portable computer. The temperature radio signal was transmitted from the child in her own bedroom, through two walls, to the plug-in receiver placed on a piece of furniture in the parents bedroom. The recording was made on the second floor of a wooden house in the center of a city of 100,000 inhabitants. The data presented in FIGS. 6A–B happen to illustrate in a single night most of the events that can occur during the skin temperature monitoring of the present invention.

The periods of all consecutive temperature pulses, i.e. the raw data, are shown in FIG. 6A. Most periods are about 42 s, longer than the 10 s FCC limit discussed above. A significant number of periods occur at multiples of this value (84, 126, etc.), corresponding to pulses that were missed by the receiver (false negatives), for any reason. It is likely that most of the early ones were obliterated by transmissions by other transmitters on the same frequency, a kind of interference that generally peaks during evening hours. However, there are very few, if any, periods resulting from extra pulses (false positives), presumably because 20 ms duration pulses are uncommon, for reasons explained above.

The resulting skin temperature profile is shown in FIG. 6B, using a 9 bin wide running median to smooth the raw period data. Temperature accuracy is better than 0.3° F. between 96° and 106° F., but it can be seen that even an accuracy of 1° F. would be sufficient for a successful operation. The first temperature drop at Hour #1 (9 pm) resulted from a diaper change and transferring the transmitter from one diaper to another. This occurred during a first skin temperature rise up to nearly 101° F., which did trip the alarm, which was set at 100° F. A second and spectacular fever flare of 105.4° F. (40.7° C.) occurred shortly after Hour #2 (10 pm). In this instance active vasodilatation brings the skin temperature very close to the core temperature, and illustrates the suitability of the method to detect fever. The temperature drop at Hour #3 (11 pm) is a loss of transmission artifact probably due to the child having moved in a position creating a poor geometrical relationship between transmitter and receiver antennas (extinction). Any low temperature alarm would easily detect that anomaly. Shortly before Hour #7 (3 am), the child woke up and cried, at which time the parents brought her in their bedroom for the rest of the night. The room transfer caused a number of false negatives. At Hour #9 (5 am) an unusually shaped temperature drop, easily detectable by a low temperature alarm of 95° F., suggests that a gap occurred between top of diaper—and transmitter attached to it—and skin. If not set tight at the beginning of the night, diapers tend to get loose with time and movement; a transmitter pasted to the skin with tape would not show this type of incident. Finally, the child woke up at 7:30 am and the transmitter was removed from contact with the skin.

It is worth noting that any event is detected with a delay of half a time width of the running median, about 3 minutes in the data shown. This is of little consequence in monitoring fevers, given their normally slow time course. Also, the higher the temperature, the shorter the periods, and the shorter the delay. With the computer plug-in receiver embodiments, temperature profiles such as FIG. 6B can easily be shown in "real time" on the computer screen concurrently with numeric values and alarm clock settings, so as to inform parents at a glance about the skin temperature history of their child. The data may also be saved to a storage medium such as a diskette to be replayed in detail for a physician, should it be necessary, for diagnostic or therapeutic purposes.

CONCLUSION, RAMIFICATIONS, AND SCOPE

Thus the reader will see that the temperature telemetry and alarm clock of the present invention provides a safe, reliable, yet economical device that can dramatically ease the monitoring of fever or diabetes in home settings. While the above description and operation contains many specificities, these should not be construed as limitations on the scope of the invention, but rather as an exemplification of a few embodiments thereof. Many other variations are possible, and will now be listed.

It will be apparent to a Health Professional that the temperature transmitter of the present invention can be positioned in other skin locations than the described abdominal area, such as thoracic, neck, axillar, or wrist areas. It will also be apparent that the described transmitter of skin temperature can be exchanged for one with other temperature objectives than fever monitoring or insulin shock detection. For example, an ovulation detector transmitter used for contraception or fertility purposes (McCreesh et al. 1996) can naturally be used with the telemetry receiver and alarm clock of the present invention, albeit with a different time scale. It will be apparent to a Physiologist or Veterinarian that the telemetry of the present invention may be used with any homeotherm in which skin vasomotricity can regulate temperature.

It will be apparent to a Chemistry Engineer that the temperature telemetry and alarm clock of the present invention can be used both to monitor the temperature of an ongoing chemical or physical process and to modify or terminate that process at a predetermined time. Generally, the receiver and alarm clock of the present invention can be used with any transmitter broadcasting period-encoded or interpulse-encoded signals.

It will be apparent to a Medical Sensors Engineer that astable 11 in transmitters 10A–B (FIGS. 1A–B) can be replaced by any other electronic device similarly producing a relatively long-period pulse as a function of temperature. It will also be apparent to an Electronics Engineer that monostable 14 in transmitter 10A (FIG. 1A) can be replaced by any encoder producing a more complex pattern than plain single pulses, with appropriate decoding on the receiving end, should it be required because of an excessive number of "false positives". However, this did not appear to be necessary in field trials.

It will be apparent to a Radio Engineer that the wire antennas described herein can be replaced alternatively by base-load, whip, coil, loop, split-ring, dipole, or rigid or flexible PCB trace antennas. Also, antenna output limiting resistors that may be required for FCC compliance are not shown in the Figures.

It will be apparent to a Computer Engineer that the typical parallel and serial port receivers described can be adapted to practically any computer port, including game, keyboard, mouse, accessory, infrared, docking, and the like.

Accordingly, the scope of the invention should be determined not by the embodiments illustrated, but by the appended claims and their legal equivalents.

It is claimed:

1. A temperature telemetry and alarm clock combination comprising;
    (a) a radio transmitter periodically transmitting a generally brief signal, whose relatively long period is a function of a measured temperature,
    (b) an alarm clock, as a functional unit that keeps the time of day, that can show the time of day on a display, that has a settable alarm time, and that can sound an alarm when the time of day reaches the set alarm time,
    (c) a radio receiver able to receive and condition said signal from said transmitter,
    (d) a programmable computing device, functionally connected to said alarm clock and said radio receiver, running an algorithm that determines the time of occurrence of said signals, calculates the period of successive signals, decodes temperature from that period, sends the decoded temperature onto said display of said alarm clock, and triggers said sound alarm of said alarm clock when the decoded temperature crosses a presettable alarm temperature threshold,
    whereby (c) and (d) synergetically share a significant number of common parts with (b), thereby lowering the overall expense of remotely monitoring the temperature data sent by (a).

2. The combination of claim 1 wherein said computing device triggers said alarm both when the temperature exceeds a high threshold and when the temperature drops below a low threshold, whereby confining allowed temperature excursions within preset limits, thereby providing a fail-safe attribute for said transmitter in case the transmitter fails or the radio transmission is interrupted for any reason.

3. The combination of claim 1 wherein said alarm clock, said radio receiver, and said computing device can be uninterruptably powered from a back-up battery in case of primary power failure, whereby all alarm functions are still operational, thereby providing a fail-safe attribute for said receiver.

4. The combination of claim 1 wherein said measured temperature is a human temperature, thereby allowing the remote monitoring of a physiological or medical condition.

5. The combination of claim 4 wherein said human temperature is a generally proximal skin temperature, whereby the temperature of the skin is numerically close to core temperature when the skin is subjected to vasodilatation, thereby allowing the remote monitoring of fevers.

6. The combination of claim 5 wherein said radio transmitter is generally of a flat low profile design with rounded edges, comprises an antenna too short to present a strangulation hazard, and is powered by a purposely large diameter flat battery to limit choking hazard should that battery get accidentally dislodged, thereby providing child-safe attributes for monitoring the temperature of infants.

7. The combination of claim 4 wherein said human temperature is a generally distal skin temperature, whereby the temperature of the skin tends to drop when the skin is subjected to peripheral vasoconstriction, thereby allowing the remote detection of iatrogenic hypoglycemia.

8. The combination of claim 4 wherein said radio transmitter comprises a magnetically actuated power switch, whereby said transmitter can be turned off by an appropriate magnetic field when not in use, thereby enabling the manufacture of a sealed waterproof dustproof unit.

9. The combination of claim 1 wherein said duration of said signal is less than 0.1 second and wherein said period of said signal is more than 10.1 seconds, whereby affording significant yet legal transmitting power while not requiring a license for the user, thereby providing the ability to monitor temperature within the boundaries of private home settings.

10. The combination of claim 9 wherein said radio transmitter further comprises a temperature or thermal switch, whereby the radio transmission is suspended when said periods shorten excessively, thereby remaining legal in extreme temperature conditions.

11. The combination of claim 1 wherein the successive periods calculated by said computing device are algorithmically smoothed prior to their decoding into temperatures, whereby filtering out false positives and false negatives stemming from interference and momentary transmission loss, thereby reducing the number of false alarms.

12. The combination of claim 11 wherein a multi-bin running median method is used to smooth the periods, whereby necessitating low computational needs and yet affording high noise rejection, thereby allowing said computing device to be of a simple inexpensive type.

13. The combination of claim 1 wherein said alarm clock, said radio receiver, and said computing device are positioned together within a same stand-alone enclosure, whereby providing a convenient dual-purpose apparatus sharing many common components, thereby enabling bedside monitoring of a temperature.

14. The combination of claim 13 wherein said enclosure further comprises a receptacle for storing said transmitter, thereby said transmitter can be protected when temperature telemetry functions are not in use.

15. The combination of claim 14 wherein said enclosure further comprises a contact switch, whereby said computing device is informed of the presence or absence of said transmitter within said receptacle, thereby said computing device can appropriately and automatically start or stop its temperature processing functions.

16. The combination of claim 14 wherein said enclosure further comprises a permanent magnet, whereby creating a magnetic field in said receptacle, thereby allowing changing of the state of a magnetically actuable switch in a removable device when this device is placed within said receptacle.

17. The combination of claim 1 wherein said radio receiver is plugged in a port of said computing device selected from the group consisting of portable, palmtop, laptop, desktop, personal digital assistants, and personal computers, wherein said computing device runs an alarm clock program, whereby affording a minimum number of components, thereby further lowering the overall expense of the temperature telemetry system.

18. A device combining both a temperature telemetry receiver and an alarm clock that share the following elements;

an electrical circuitry keeping time and able to measure time intervals, a numeric display, both of the time of day and of telemetered temperature, shown either simultaneously or successively, a noise producing alarm selected from the group consisting of loudspeakers, vibrators, bells, and buzzers, a plurality of buttons or switches to set time and temperature alarms, and to stop said alarms, a back-up fail-safe battery to ensure that said alarms would be triggered should a primary source of electrical power fail, and that further comprises a telemetry radio receiver and associated signal and data processing circuitry to receive and decode temperature readings sent by a remotely situated telemetry transmitter, thereby providing a multipurpose and convenient means to monitor and periodically supervise the temperature of a child or adult patient, especially at night.

19. The combination of claim 18, further comprising a receiver for a commercial broadcast band, whereby more components can be shared between telemetry receiver, broadcast receiver, and alarm clock.

* * * * *